United States Patent
Yamada et al.

(10) Patent No.: US 7,335,783 B2
(45) Date of Patent: Feb. 26, 2008

(54) THIN FILM-FORMING MATERIAL AND METHOD FOR PRODUCING THIN FILM

(75) Inventors: Naoki Yamada, Tokyo (JP); Shinichi Tanaka, Tokyo (JP)

(73) Assignee: Adeka Corporation, Tokyo (JP)

( * ) Notice: Subject to any disclaimer, the term of this patent is extended or adjusted under 35 U.S.C. 154(b) by 0 days.

(21) Appl. No.: 11/628,850

(22) PCT Filed: May 31, 2005

(86) PCT No.: PCT/JP2005/009932

§ 371 (c)(1), (2), (4) Date: Dec. 8, 2006

(87) PCT Pub. No.: WO2005/121401

PCT Pub. Date: Dec. 22, 2005

(65) Prior Publication Data

US 2007/0178235 A1    Aug. 2, 2007

(30) Foreign Application Priority Data

Jun. 14, 2004   (JP) .............................. 2004-175122

(51) Int. Cl.
   *C07F 3/06*   (2006.01)
   *C23C 16/06*  (2006.01)
(52) U.S. Cl. ................ 556/40; 556/130; 427/255.33
(58) Field of Classification Search ................ 556/40, 556/130; 427/255.33
   See application file for complete search history.

(56) References Cited

U.S. PATENT DOCUMENTS 5,258,204 A * 11/1993 Wernberg et al. ....... 427/255.19
5,980,983 A * 11/1999 Gordon ...................... 427/226

FOREIGN PATENT DOCUMENTS

| JP | 6-064738 | 8/1994 |
| JP | 6-316440 | 11/1994 |
| JP | 08-003171 | 1/1996 |
| JP | 2000-212744 | 8/2000 |
| JP | 2001-181840 | 7/2001 |
| JP | 2002-309373 | 10/2002 |
| JP | 2003-64019 | 3/2003 |
| JP | 2003-236376 | 8/2003 |
| WO | WO 98/46617 | 10/1998 |

OTHER PUBLICATIONS

Kamisuki et al., "Preparation and Properties of Pb(Zn1/3Nb2/3)O3-PbTiO3 Thin Films by Metalorganic Chemical Vapor Deposition," *Microelectron Engineering*, vol. 29, 1995, pp. 169-172.

* cited by examiner

*Primary Examiner*—Porfirio Nazario-Gonzalez
(74) *Attorney, Agent, or Firm*—Young & Thompson

(57) ABSTRACT

The thin film-forming material of the present invention comprises a bis(β-diketonato)zinc compound that is liquid at 25° C. and is suitable for forming a zinc-containing thin film. By using the thin film-forming material, a thin film can be produced with stable film-forming rate or stable film composition control without suffering from problems of raw material gas suppliability and in-line raw material transport. Preferred (β-diketonato)zinc compounds are bis(octane-2,4-dionato)zinc and bis(2,2dimethyl-6-ethyldecane-3,5-dionato) zinc.

7 Claims, 3 Drawing Sheets

THIN FILM-FORMING MATERIAL AND METHOD FOR PRODUCING THIN FILM

TECHNICAL FIELD

The present invention relates to a thin film-forming material comprising a bis(β-diketonato)zinc that is liquid at 25° C. and a method for producing a thin film using this material.

BACKGROUND ART

A thin film containing zinc has various characteristics such as optical characteristics, electrical characteristics, catalytic activity, and the like, and is used as a member in electronics parts and optical parts.

Methods for producing the above-mentioned thin film include flame deposition, sputtering, ion-plating, MOD processes such as coating thermal decomposition, sol-gel process and the like, chemical vapor deposition, and others. Chemical vapor deposition (hereinafter may be simply described as CVD) including ALD (Atomic Layer Deposition) is the most suitable production process owing to many advantages such as excellence in controllability of compositions and step coverage, suitability for large-scale production, capability of hybrid integration, and the like.

In the CVD processes, β-diketonate complexes excellent in stability and safety have been used as precursors supplying zinc to a thin film. For example, Patent Documents 1 to 3 reported methods for producing zinc-containing thin films using bis(pentane-2,4-dionato)zinc, and Non-patent Document 1 reported a method for producing zinc-containing thin films using bis(2,2,6,6-tetramethylheptane-3,5-dionato)zinc. However, since these complexes are solid, they are required to be either vaporized by sublimation or kept at high temperatures not lower than the melting points thereof in the step of vaporization of the raw materials, and there have been problems in supplying the raw material gas, such as insufficient amount of vaporization or temporal variation of vaporization, and problems in in-line raw material transport. Further, in the solution CVD process using a solution in which a solid precursor is dissolved in an organic solvent, the solid precursor is likely to precipitate due to variation of temperature, partial evaporation of the solvent or variation in concentration of the solution in the vaporization equipment, resulting in temporal variation of feed rate through clogging in feed lines or the like. Hence, there is a problem that it is impossible to produce a thin film with stable film-forming rate or stable thin film composition control.

In order to circumvent these problems, Patent Document 4 reported a method of using a liquid β-diketonate containing a mixture of two or more kinds of β-diketones. Due to use of a mixture, however, this method still has problems in stability of conditions in producing a thin film and solid precipitation.

Patent Document 1: Japanese Patent Application Publication No. H6-64738
Patent Document 2: Japanese Patent Laid-open Publication No. H8-3171
Patent Document 3: Japanese Patent Laid-open Publication No. 2003-236376
Patent Document 4: Pamphlet of WO98/46617
Non-patent Document 1: Microelectron. Eng., 29(14), 16972(1995)

DISCLOSURE OF THE INVENTION

Problems to be Solved by the Invention

An object of the present invention is to provide a thin film-forming material that contains a zinc compound and is suitable for forming a zinc-containing thin film.

Means for Solving the Problems

The present inventors have found, as a result of their intensive investigation, that a specific zinc compound that is liquid by itself is useful for a thin film-forming material and that the above object can be achieved using this compound.

The present invention is based on the above findings and provides a thin film-forming material comprising a bis(β-diketonato)zinc compound that is liquid at 25° C. and a method for producing a thin film using the thin film-forming material by a chemical vapor deposition process.

BEST MODE FOR CARRYING OUT THE PRESENT INVENTION

Figure 1:
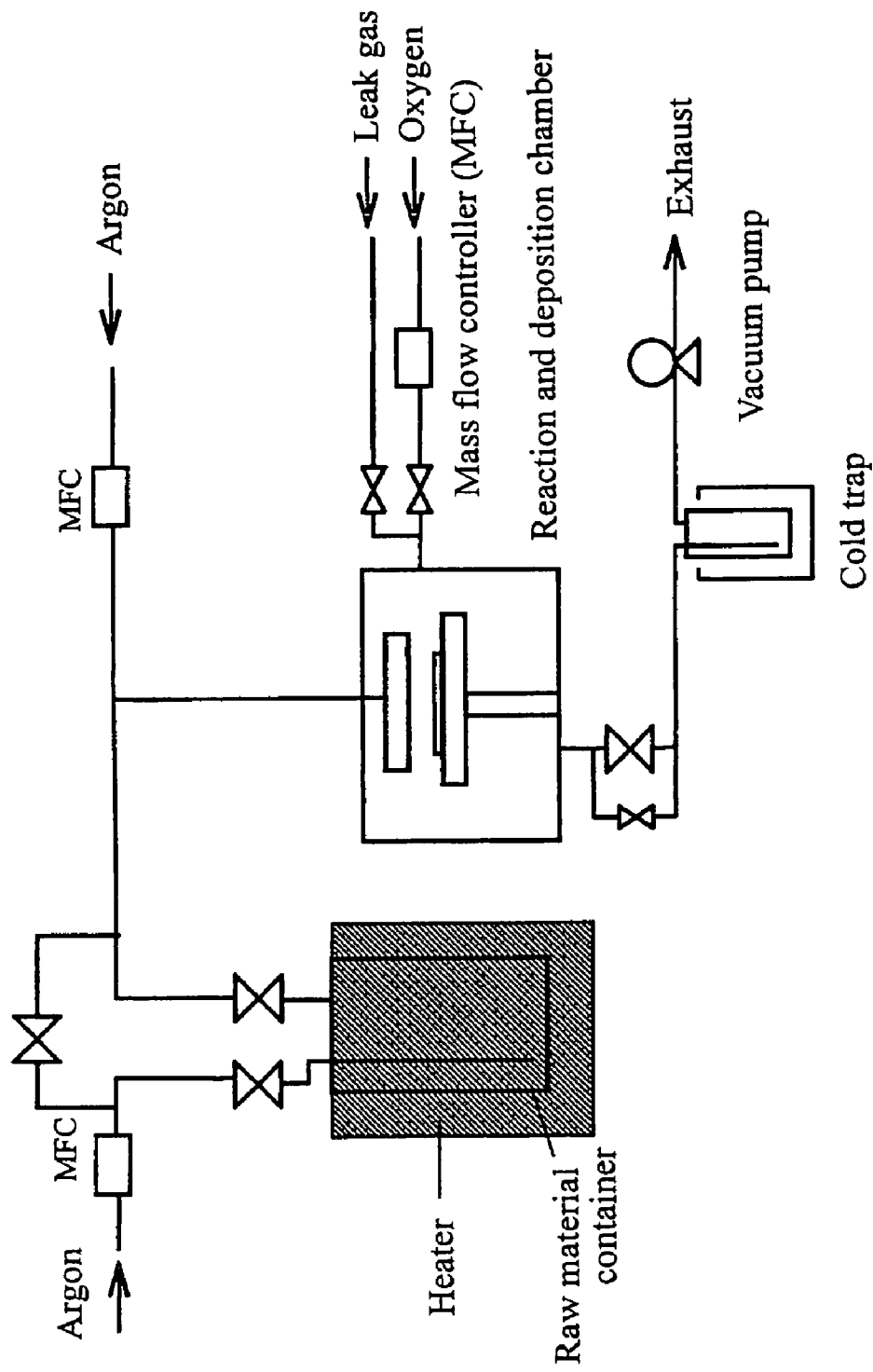
FIG. 1 is a schematic view showing an example of a CVD apparatus used in the method for producing a thin film of the present invention.

The bis(β-diketonato)zinc compound relating to the present invention is a complex in which two β-diketone residues bond to one zinc atom. The two β-diketone residues coordinating to the zinc atom may be the same or different and may have an optically active site therein.

The thin film-forming material of the present invention comprises the above bis(β-diketonato)zinc compound as a precursor for a forming thin film and may either consist of only the bis(β-diketonato)zinc compound or contain other components such as organic solvents or the like as appropriate according to purposes, as described later.

A thin film formed from the thin film-forming material of the present invention can be provided as any kind of thin film such as metals, alloys, sulfides, oxide ceramics, nitride ceramics, glass, and the like as desired by appropriately selecting precursors of other components, reactive gases, and conditions in production. The kinds of producible thin film include, for example, zinc, ZnSe, zinc oxide, zinc sulfide, zinc-indium complex oxide, Li-doped zinc oxide, zinc-doped ferrite, lead-zinc complex oxide, lead-zinc-niobium complex oxide, bismuth-zinc-niobium complex oxide, and barium-zinc-tantalum complex oxide. Applications of these thin films include, for example, transparent conductors, emitters, fluorophores, photocatalysts, magnetic substances, conductors, highly dielectric materials, ferroelectrics, piezoelectric materials, microwave dielectric materials, optical waveguides, optical amplifiers, optical switches, and the like.

The bis(β-diketonato)zinc compound relating to the present invention is liquid at 25° C. and therefore it is useful as a thin film-forming material in the following points.

In CVD processes including the ALD process, there is no temporal variation in the feed rate caused by clogging in feed lines or the like, and therefore thin film production with stable film-forming rate or stable thin film composition control. In addition, in the process of producing thin film-forming materials, operations such as syntheses, purification, transporting and filling of liquids and the like become easier.

As for bis(β-diketonato)zinc compounds known as a precursor of a thin film-forming material, the melting point of bis(pentane-2,4-dionato)zinc is around 137° C., the melting point of bis(2,2,6,6-tetramethylheptane-3,5-dionato)zinc is around 142° C., and the melting point of bis(2,6-dimethylheptane-3,5-dionato)zinc is around 82° C.

In MOD processes, if the precursor is solid, nonuniformity in coating or pinholes may be brought about due to precipitation on applying a solution of the precursor serving as a thin film-forming material. Further, if the precursor is solid, solid may be precipitated on storage of the solution of the precursor serving as a thin film-forming material. Because the bis(β-diketonato)zinc compound relating to the present invention is liquid at 25° C., these problems can be circumvented and the concentration of the precursor in the thin film-forming material can be set in a wide range extending to higher values.

Accordingly, among the bis(β-diketonato)zinc compounds relating to the present invention, a compound with larger fluidity is more valuable. Specifically, a compound having a viscosity at 25° C. of 2000 mPa·s or less is preferred. In the production of a thin film-forming material and in a CVD process, the feed line may be warmed to increase the fluidity of the bis(β-diketonato)zinc compound relating to the present invention. In this case, a compound that exhibits large fluidity with warming as mild as possible is advantageous. Specifically, a compound having a viscosity at 50° C. of 200 mPa·s or less is preferred.

As bis(β-diketonato)zinc compounds exhibiting preferable viscosity described above, there may be mentioned, for example, bis(octane-2,4-dionato)zinc and bis(2,2-dimethyl-6-ethyldecane-3,5-dionato)zinc.

As the method for producing the bis(β-diketonato)zinc compound relating to the present invention, well-known common synthetic methods for β-diketone-metal complexes without particular limitations can be used. For example, it may be produced by reaction of a zinc salt (an inorganic salt such as chloride, bromide, iodide, nitrate, sulfate, and the like; or a salt with an organic acid such as acetic acid and the like) or a hydrate thereof with the corresponding β-diketone compound in the presence of a base such as sodium hydroxide, ammonia, an amine and the like. Alternatively, it may be produced by exchange reaction of a zinc alkoxide derived from a lower alcohol (methoxide, ethoxide, isopropoxide, butoxide, etc.) or a lower organic amide (dimethylamide, diethylamide, dibutylamide, etc.) of zinc with the corresponding β-diketone compound.

The embodiment of the thin film-forming material of the present invention depends on the production process (for example, frame deposition, sputtering, ion-plating, MOD processes such as coating thermal decomposition, sol-gel process, and the like, CVD process including ALD process) of the thin film to which the thin film-forming material is applied. Since the bis(β-diketonato)zinc compound relating to the present invention is easily vaporized, the thin film-forming material of the present invention is particularly valuable as a material for chemical vapor deposition.

When the thin film-forming material of the present invention is a material for chemical vapor deposition (CVD), the embodiment is appropriately selected according to the operation mode such as the delivery system and the like in the CVD process to be used.

The delivery system includes a vapor transporting system in which a material for CVD is vaporized through heating and/or pressure reduction in a raw material container, and the vapor is introduced into a deposition reaction chamber, together with a carrier gas such as argon, nitrogen, helium, and the like if necessary; a liquid transporting system in which a material for CVD in a liquid or solution state is transported to a vaporizer and vaporized through heating and/or pressure reduction in the vaporizer, and the vapor is introduced into a deposition reaction chamber. In the case of the vapor transporting system, the material for CVD is the bis(β-diketonato)zinc compound relating to the present invention per se, while in the case of the liquid-transporting system, the material for CVD is the neat bis(β-diketonato) zinc compound relating to the present invention or a solution in which the zinc compound is dissolved in an organic solvent.

In a multi-component CVD process, there are a system in which individual components of the material for CVD are separately vaporized and supplied (hereinafter, may be described as "single source system") and a system in which a mixed raw material prepared by premixing a plurality of raw material components at a desired composition is vaporized and supplied (hereinafter, may be described as "cocktail source system"). In the case of the cocktail source system, the material for CVD is a mixture of the bis(β-diketonato) zinc compound relating to the present invention and a metal compound(s) serving as (an)other precursor(s), or a solution wherein these compounds are dissolved in an organic solvent.

As the organic solvent used in the material for CVD, well-known common organic solvents can be used without any particular limitations. The organic solvent includes, for example, alcohols such as methanol, ethanol, 2-propanol, n-butanol, and the like; acetates such as ethyl acetate, butyl acetate, methoxyethyl acetate, and the like; ether alcohols such as ethylene glycol monomethyl ether, ethylene glycol monoethyl ether, ethylene glycol monobutyl ether, diethylene glycol monomethyl ether, and the like; ethers such as tetrahydrofuran, tetrahydropyran, ethylene glycol dimethyl ether, diethylene glycol dimethyl ether, triethylene glycol dimethyl ether, dibutyl ether, and the like; ketones such as methyl butyl ketone, methyl isobutyl ketone, ethyl butyl ketone, dipropyl ketone, diisobutyl ketone, methyl amyl ketone, cyclohexanone, methylcyclohexanone, and the like; hydrocarbons such as hexane, cyclohexane, methylcyclohexane, dimethylcyclohexane, ethylcyclohexane, heptane, octane, toluene, xylene, and the like; cyano group-containing hydrocarbons such as 1-cyanopropane, 1-cyanobutane, 1-cyanohexane, cyanocyclohexane, cyanobenzene, 1,3-dicyanopropane, 1,4-dicyanobutane, 1,6-dicyanohexane, 1,4-dicyanocyclohexane, 1,4-dicyanobenzene, and the like; pyridine, and lutidine. These solvents are used alone or in a combination of two or more according to solubility of solutes, relationship of the temperature in use with the boiling points and flash points, and other conditions. When such an organic solvent is used, it is preferred that the total amount of the bis(β-diketonato)zinc compound and (an) other precursor(s) is 0.01 to 2.0 mol/L, particularly 0.05 to 1.0 mol/L in the organic solvent.

As other precursors used together with the bis(β-diketonato)zinc compound relating to the present invention in a multi-component CVD process, well-known common precursors used as materials for CVD may be used without any particular limitations.

Other precursors include, for example, a compound composed of a metal and one kind or two or more kinds of organic ligands selected from alcoholic compounds, glycolic compounds, β-diketone compounds, cyclopentadiene compounds and organic amine compounds; alkylmetal compounds; and arylmetal compounds. The metal in the precursor includes, for example, magnesium, calcium, strontium, barium, titanium, zirconium, hafnium, vanadium, niobium, tantalum, manganese, iron, ruthenium, cobalt, rhodium, iridium, nickel, palladium, platinum, copper, silver, gold, gallium, indium, germanium, tin, lead, antimony, bismuth, silicon, yttrium, lanthanum, cerium, praseodymium, neodymium, promethium, samarium, europium, gadolinium, terbium, dysprosium, holmium, erbium, thulium, and ytterbium.

The alcoholic compound used as the organic ligand includes alkanols such as methanol, ethanol, propanol, isopropanol, butanol, 2-butanol, isobutanol, tert-butanol, amyl alcohol, isoamyl alcohol, tert-amyl alcohol, and the like; ether alcohols such as 2-methoxyethanol, 2-ethoxyethanol, 2-butoxyethanol, 2-(2-methoxyethoxy)ethanol, 2-methoxy-1-methylethanol, 2-methoxy-1,1-dimethylethanol, 2-ethoxy-1,1-dimethylethanol, 2-isopropxy-1,1-dimethylethanol, 2-butoxy-1-1-dimethylethanol, 2-(2-methoxyethoxy)-1,1-dimethylethanol, 2-propoxy-1,1-diethylethanol, 2-sec-butoxy-1,1-diethylethanol, 3-methoxy-1,1-dimethylpropanol, and the like; dialkylaminoalcohols; and the like.

The glycolic compound used as the organic ligand includes 1,2-ethanediol, 1,2-propanediol, 1,3-propanediol, 2,4-hexanediol, 2,2-dimethyl-1,3-propanediol, 2,2-diethyl-1,3-propanediol, 1,3-butanediol, 2,4-butanediol, 2,2-diethyl-1,3-butanediol, 2-ethyl-2-butyl-1,3-propanediol, 2,4-pentanediol, 2-methyl-1,3-propanediol, 2-methyl-2,4-pentanediol, 2,4-hexanediol, 2,4-dimethyl-2,4-pentanediol, and the like.

The β-diketone compound used as the organic ligand includes alkylated β-diketones such as acetylacetone, hexane-2,4-dione, 5methylhexane-2,4-dione, heptane-2,4-dione, 2-methylheptane-3,5dione, 5methylheptane-2,4-dione, 6-methylheptane-2,4-dione, 2,2-dimethylheptane-3,5dione, 2,6-dimethylheptane-3,5dione, 2,2,6-trimethylheptane-3,5dione, 2,2,6,6-tetramethylheptane-3,5dione, octane-2,4-dione, 2,2,6-trimethyloctane-3,5dione, 2,6-dimethyloctane-3,5dione, 2,9-dimethylnonane-4,6-dione, 2-methyl-6-ethyldecane-3,5dione, 2,2-dimethyl-6-ethyldecane-3,5dione, and the like; fluorinated β-diketones such as 1,1,1-trifluoropentane-2,4-dione, 1,1,1-trifluoro-5,5dimethylhexane-2,4-dione, 1,1,1,5,5,5hexafluoropentane-2,4-dione, 1,3-diperfluorohexylpropane-1,3-dione, and the like; ether-substituted β-diketones such as 1,1,5,5 tetramethyl-1-methoxyhexane-2,4-dione, 2,2,6,6-tetramethyl-1-methoxyheptane-3,5dione, 2,2,6,6-tetramethyl-1-(2-methoxyethoxy)heptane-3,5dione, and the like; and others.

The cyclopentadiene compound used as the organic ligand includes cyclopentadiene, methylcyclopentadiene, ethylcyclopentadiene, propylcyclopentadiene, isppropylcyclopentadiene, butylcyclopentadiene, sec-butylcyclopentadine, isobutylcyclopentadiene, tert-butylcyclopentadiene, dimethylcyclopentadiene, tetramethylcyclopentadiene, and the like.

The organic amine compound used as the organic ligand includes methylamine, ethylamine, propylamine, isopropylamine, butylamine, sec-butylamine, tert-butylamine, isobutylamine, dimethylamine, diethylamine, dipropylamine, diisopropylamine, ethylmethylamine, propylmethylamine, isopropylmethylamine, and the like.

The alkyl group in the alkylmetal compound includes methyl, ethyl, propyl, isopropyl, butyl, sec-butyl, tert-butyl, isobutyl, pentyl, tert-pentyl, isopentyl, and the like. The aryl group in the arylmetal compound includes phenyl, methylphenyl, dimethylphenyl, ethylphenyl, and the like.

The thin film-forming material of the present invention may contain a nucleophile in order to stabilize the bis(β-diketonato)zinc compound relating to the present invention and (an)other precursor(s), if necessary. The nucleophile includes ethylene glycol ethers such as glyme, diglyme, triglyme, tetraglyme, and the like; crown ethers such as 18-crown-6, dicyclohexyl-18-crown-6, 24-crown-8, dicyclohexyl-24-crown-8, dibenzo-24-crown-8, and the like; polyamines such as ethylenediamine, N,N'-tetramethylethylenediamine, diethylenetriamine, triethylenetetramine, tetraethylenepentamine, pentaethylenehaxamine, 1,1,4,7,7-pentamethyldiethylenetriamine, 1,1,4,7,10,10-hexamethyltriethylenetetramine, and the like; cyclic polyamines such as cyclam, cyclen, and the like; β-ketoesters such as methyl acetoacetate, ethyl acetoacetate, 2-methoxyethyl acetoacetate, and the like; and δ-diketones such as acetylacetone, 2,4-hexanedione, 2,4-heptanedione, 3,5heptanedione, dipivaloylmethane, and the like. The amount of such a nucleophile used added as a stabilizer is typically in a range of 0.1 mol to 10 mol, preferably 1 to 4 mol, with respect to 1 mol of the precursor(s).

In the method for producing a thin film of the present invention, the thin film is produced using the thin film-forming material of the present invention as a material for CVD, wherein vapor containing the zinc compound obtained by vaporizing the thin film-forming material of the present invention, vapor obtained by vaporizing (an)other precursor(s) used as necessary, and a reactive gas used as necessary are introduced onto a substrate, and the precursor(s) is(are) subsequently allowed to decompose and/or react over the substrate so that the product is deposited and grown as a thin film on the substrate. There are no particular limitations on the raw material delivery system, deposition mode, production conditions, production apparatus, and the like. Well-known conditions, modes, and the like may be employed.

The reactive gas used as necessary includes, for example, as an oxidizing gas, oxygen, ozone, nitrogen dioxide, nitrogen monoxide, steam, hydrogen peroxide, formic acid, acetic acid, acetic anhydride, and the like; as a reducing gas, hydrogen; and as a source for producing a nitride, organic amine compounds such as monoalkylamines, dialkylamines, trialkylamines, alkylenediamines, and the like, hydrazine, ammonia, and the like.

The delivery system includes the vapor transporting system, liquid transporting system, single source system, and cocktail source system described above and others.

The deposition mode includes thermal CVD in which only heat is used to cause a reaction of the raw material gas, or the raw material gas and the reactive gas to deposit a thin film, plasma-enhanced CVD in which heat and plasma are used, the photo-assisted CVD in which heat and light are used, photo plasma-assisted CVD in which heat, light, and plasma are used, and ALD (Atomic Layer Deposition) in which the deposition reaction in the CVD process is separated into elementary steps and deposition is performed stepwise at a molecular level.

The production conditions include the reaction temperature (the temperature of the substrate), the reaction pressure, the deposition rate, and the like. The reaction temperature is preferably 160° C. or more, at which the bis(β-diketonato) zinc compound relating to the present invention is sufficiently reactive, and more preferably 250 to 800° C. The reaction pressure is preferably an atmospheric pressure to 10 Pa for thermal CVD or photo-assisted CVD, while it is preferably 10 to 2000 Pa when plasma is used. The deposition rate can be controlled by the raw material feed conditions (vaporizing temperature, vaporizing pressure), the reaction temperature, and the reaction pressure. When the deposition rate is too high, the characteristics of the resultant thin film may be deteriorated, while too low deposition rate may result in poor productivity. Accordingly, the deposition rate is preferably 0.5 to 5000 nm/min, and more preferably 1 to 1000 nm/min. In the case of ALD, the film thickness is controlled by the number of cycles to reach a desired film thickness.

In the method for forming a thin film of the present invention, after deposition, the thin film may be annealed to improve electrical characteristics. If step coverage is required, a step of reflowing the thin film may be provided. The temperature in reflowing is typically 500 to 1200° C., and preferably 600 to 800° C.

A thin film formed by the method for forming a thin film of the present invention using the thin film-forming material of the present invention, as described above, can be provided in any kind of thin film including metals, alloys, sulfides, oxide ceramics, nitride ceramics, glass, and the like as desired by selecting precursors of other components, reactive gases, and production conditions as appropriate. The kinds of producible thin film include, for example, zinc, ZnSe, zinc oxide, zinc sulfide, zinc-indium complex oxide, Li-doped zinc oxide, zinc-doped ferrite, lead-zinc complex oxide, lead-zinc-niobium complex oxide, bismuth-zinc-niobium complex oxide, and barium-zinc-tantalum complex oxide. Applications of these thin films include, for example, transparent conductors, emitters, fluorophores, photocatalysts, magnetic substances, conductors, highly dielectric materials, ferroelectrics, piezoelectric materials, microwave dielectric materials, optical waveguides, optical amplifiers, optical switches, and the like.

EXAMPLES

Hereinafter, the present invention will be described in more detail with reference to Production Examples and Examples. However, the present invention is not limited by these examples.

Production Example 1

Production of Bis(octane-2,4-dionato)zinc

A reaction flask filled with dry argon was charged with 1.0 mol of octane-2,4-dione, 1.0 mol of sodium hydroxide, and 1000 g of methanol dried to the extent that the water content was less than 5 ppm. Here was added a solution containing 600 g of methanol and 0.5 mol of zinc nitrate hexahydrate dropwise at 25° C. The resultant mixture was stirred at 25° C. for 5 hr, the solid was filtered off, and the solvent was distilled off. The resultant residue was distilled under reduced pressure to obtain 53 g (yield 30%) of a yellow liquid from a fraction at a column top temperature of 128° C. under a pressure of 20 Pa. The obtained yellow liquid was identified as the desired compound, bis(octane-2,4-dionato)zinc. The analytical results of the yellow liquid are shown below.

(Analytical Results)
(1) Elemental analyses (CH: CHN analyzer, metal analysis: ICP-MS)
C: 54.8 mass % (theoretical value 55.3%), H: 7.5 mass % (theoretical value 7.5%), and
Zn: 17.0 mass % (theoretical value 18.7%).
(2) $^1$H NMR (solvent: deuterated benzene) (chemical shift; multiplicity; number of protons)
(0.78; t; 6), (1.17; m; 4), (1.49; m; 4), (1.74; s; 6), (2.04; t; 4), (5.18; s; 2).
(3) TG-DTA (Ar 100 ml/min, temperature increasing rate 10° C./min, sample amount 11.475 mg)
Temperature at which 50 mass % was lost: 250° C.
(4) Viscosity measurement (falling sphere method using an automatic microviscometer AMVn manufactured by Anton Paar GmbH)
Viscosity at 25° C.: 336 mPa·s, Viscosity at 50° C.: 43 mPa·s.

Production Example 2

Production of bis(2,2-dimethyl-6-ethyldecane-3,5dionato)zinc

A reaction flask filled with dry argon was charged with 0.8 mol of 2,2-dimethyl-6-ethyldecane-3,5dione, 0.8 mol of sodium hydroxide, and 1000 g of methanol dried to the extent that the water content was less than 5 ppm. Here was added a solution containing 600 g of methanol and 0.4 mol of zinc nitrate hexahydrate dropwise at 25° C. The resultant mixture was stirred at 25° C. for 5 hr, the solid was removed by filtration, and the solvent was removed. The resultant residue was distilled under reduced pressure to obtain 29 g (yield 28%) of a light yellow liquid from a fraction at a column top temperature of 151° C. under a pressure of 20 Pa. The obtained light yellow liquid was identified as the desired compound, bis(2,2-dimethyl-6-ethyldecane-3,5dionato)zinc. The analytical results of the light yellow liquid are shown below.

(Analytical Results)
(1) Elemental analyses (CH: CHN analyzer, metal analysis: ICP) Zn: 13.7 mass % (theoretical value 12.7%).
(2) $^1$H NMR (solvent: deuterated benzene) (chemical shift; multiplicity; number of protons)
(0.85; m; 6), (0.90; m; 6), (1.07; s; 18), (1.33; m; 12), (1.66; m; 4), (2.04; m; 2), (5.63; s; 2).
(3) TG-DTA (Ar 100 ml/min, temperature increasing rate 10° C./min, sample amount 9.756 mg)
Temperature at which 50 mass % was lost: 267° C.
(4) Viscosity measurement (falling sphere method using an automatic microviscometer AMVn manufactured by Anton Paar GmbH) Viscosity at 25° C.: 1022 mPa·s, Viscosity at 50° C.: 118 mPa·s.

Example 1

Production of a Thin Film of Zinc Oxide

Using the apparatus shown in FIG. 1, a thin film of zinc oxide was produced on a silicon wafer under the following conditions. The film thickness and composition of the produced thin film were examined by X-ray fluorescence spectroscopy. The results are shown below.

(Conditions for Production)
Zinc-containing material for CVD: bis(octane-2,4-dionato)zinc [raw material temperature: 180° C., pressure: 666 Pa, carrier gas: argon 150 sccm], oxidizing gas: oxygen 150 sccm, reaction pressure: 666 Pa, reaction temperature (substrate temperature): 550° C., time for film formation: 20 min.

(Results)
Film thickness: 84 nm; film composition: zinc oxide

Example 2

Production of Bismuth-Zinc-Niobium Complex Oxide

Figure 2:
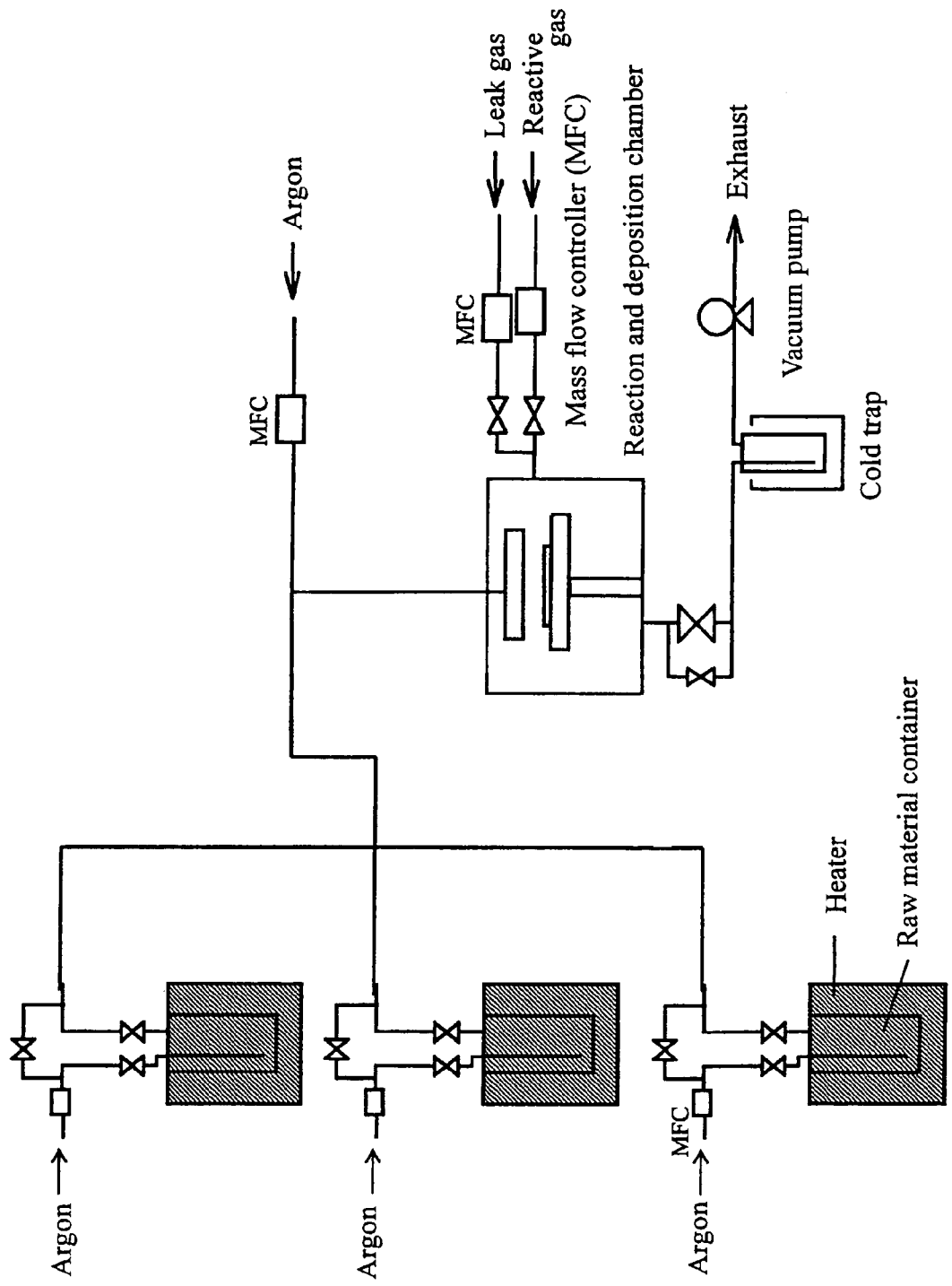
FIG. 2 is a schematic view showing an example of a CVD apparatus used in the method for producing a thin film of the present invention.

Using the apparatus for CVD shown in FIG. 2, a thin film of bismuth-zinc-niobium complex oxide was produced on a silicon wafer under the following conditions. The film thickness and composition of the produced thin film were examined by X-ray fluorescence spectroscopy. The results are shown below.

(Conditions for Production)

Bismuth-containing material for CVD: triphenylbismuth [raw material temperature: 130° C., pressure: 666 Pa, carrier gas: argon 150 sccm], zinc-containing material for CVD: bis(2,2-dimethyl-6-ethyldecane-3,5dionato)zinc [raw material temperature: 160° C., pressure: 666 Pa, carrier gas: argon 50 sccm], niobium-containing material for CVD: penta(ethoxy)niobium [raw material temperature: 120° C., pressure: 666 Pa, carrier gas: argon 100 sccm], oxidizing gas: oxygen 150 sccm, reaction pressure: 50 Pa, reaction temperature (substrate temperature): 550° C., time for film formation: 20 min.

(Results)

Film thickness: 90 nm; composition (molar ratio): Bi/Zn/Nb=1.0/0.33/0.67.

Example 3

Production of Lead-Zinc-Niobium Complex Oxide

Figure 3:
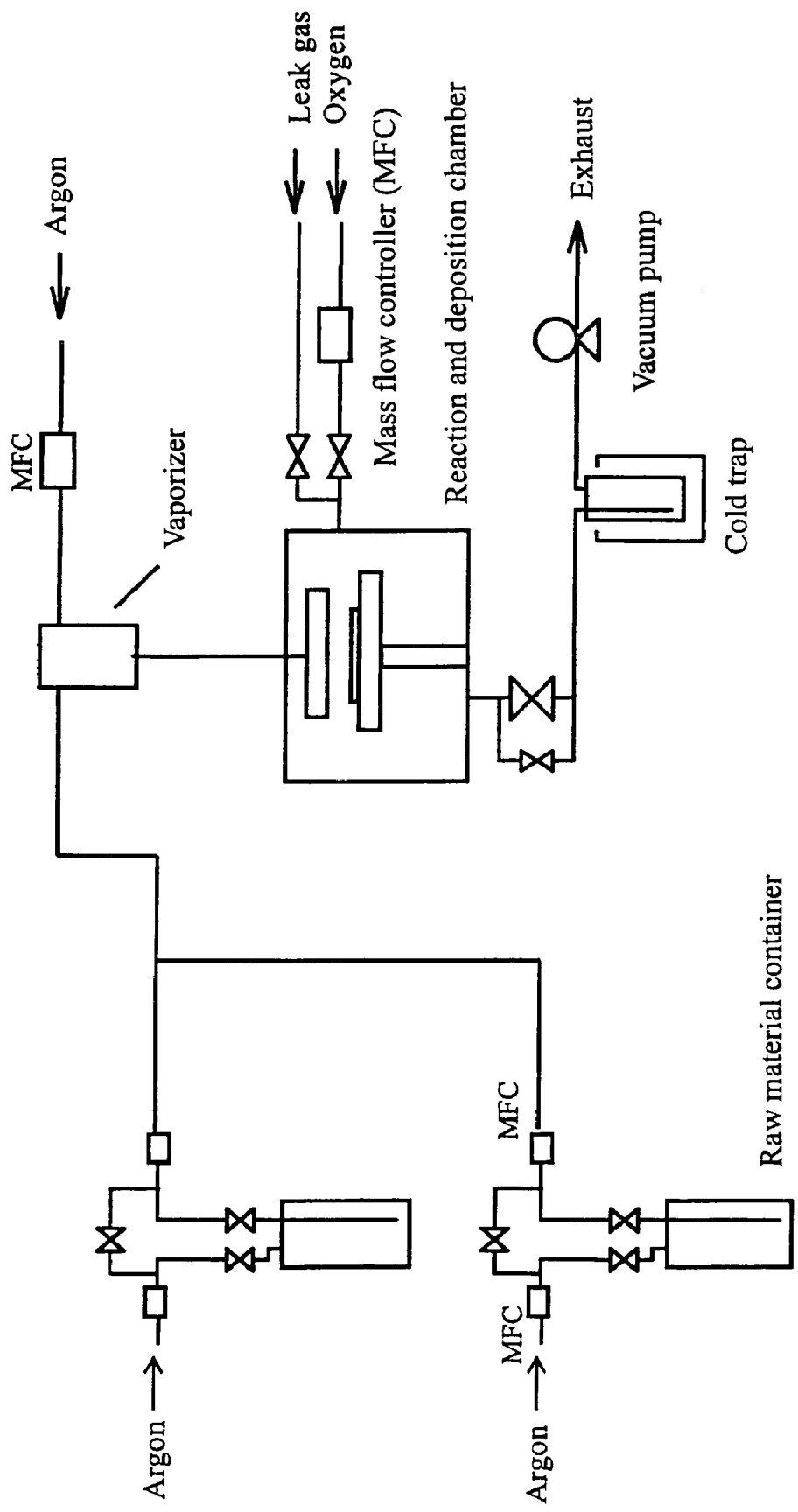
FIG. 3 is a schematic view showing an example of a CVD apparatus used in the method for producing a thin film of the present invention.

Using the apparatus for CVD shown in FIG. 3, a thin film of lead-zinc-niobium complex oxide was produced on a silicon wafer under the following conditions. The film thickness and composition of the produced thin film were examined by X-ray fluorescence spectroscopy. The results are shown below.

(Conditions for Production)

Mixed material for CVD containing lead and zinc: a mixture of a solution containing 0.06 mol/L of bis(2,2,6,6-tetramethylheptane-3,5dionato)lead in ethylcyclohexane and a solution containing 0.02 mol/L of bis(2,2-dimethyl-6-ethydecane-3,5dionato)zinc in ethylcyclohexane, niobium-containing material for CVD: penta(ethoxy)niobium, vaporizer temperature: 230° C., raw material gas flow: 50 sccm, oxygen gas flow: 350 sccm, reaction pressure: 666 Pa, reaction time: 10 min, substrate temperature: 550° C., carrier gas: argon 150 sccm.

(Results)

Film thickness: 100 nm; composition (molar ratio): Pb/Zn/Nb=1.0/0.30/0.67.

In Examples 1 to 3, it was confirmed that, by using the thin film-forming material of the present invention, a thin film can be produced with stable film-forming rate and stable film composition control without suffering from problems of raw material gas suppliability or in-line raw material transport.

INDUSTRAIL APPLICABILITY

The present invention can provide a thin film-forming material suitable for forming a zinc-containing thin film, and by using the thin film-forming material, a thin film can be produced with stable film-forming rate or stable film composition control without suffering from problems of raw material gas suppliability and in-line raw material transport.

The invention claimed is:

1. A thin film-forming material comprising bis(octane-2, 4-dionato)zinc.

2. The thin film-forming material according to claim 1, wherein the viscosity of the bis($\beta$-diketonato)zinc compound is 2000 mPa·s or less at 25° C.

3. The thin film-forming material according to claim 1, wherein the viscosity of the bis($\beta$-diketonato)zinc compound is 200 mPa·s or less at 50° C.

4. A method for producing a thin film, wherein vapor containing a zinc compound obtained by vaporizing the thin film-forming material described in claim 1 is introduced onto a substrate and the zinc compound is allowed to decompose and/or react to form a zinc-containing thin film on the substrate.

5. A method for producing a thin film, wherein vapor containing a zinc compound obtained by vaporizing the thin film-forming material described in claim 2 is introduced onto a substrate and the zinc compound is allowed to decompose and/or react to form a zinc-containing thin film on the substrate.

6. A method for producing a thin film, wherein vapor containing a zinc compound obtained by vaporizing the thin film-forming material described in claim 3 is introduced onto a substrate and the zinc compound is allowed to decompose and/or react to form a zinc containing thin film on the substrate.

7. A thin film-forming material comprising bis(2,2-dimethyl-6-ethyldecane-3, 5-dionato)zinc.

* * * * *